(12) United States Patent
Steineker

(10) Patent No.: US 7,910,358 B1
(45) Date of Patent: Mar. 22, 2011

(54) ETHANOL DISTILLATION SYSTEM

(76) Inventor: David T Steineker, Prospect, KY (US)

( * ) Notice: Subject to any disclaimer, the term of this patent is extended or adjusted under 35 U.S.C. 154(b) by 867 days.

(21) Appl. No.: 11/850,254

(22) Filed: Sep. 5, 2007

(51) Int. Cl.
*C12M 1/00* (2006.01)
*C12M 3/00* (2006.01)

(52) U.S. Cl. .................................. 435/289.1

(58) Field of Classification Search ............. 435/289.1
See application file for complete search history.

(56) References Cited

U.S. PATENT DOCUMENTS

| | | |
|---|---|---|
| 4,407,955 A | 10/1983 | Muller et al. |
| 4,460,687 A | 7/1984 | Ehnstrom |
| 4,571,534 A | 2/1986 | Cover |
| 4,952,503 A | 8/1990 | Granstedt |
| 7,326,765 B1 * | 2/2008 | Tzap et al. ............. 528/423 |
| 2002/0103548 A1 * | 8/2002 | Treiber et al. .............. 700/30 |
| 2003/0175948 A1 * | 9/2003 | Hong et al. ............. 435/289.1 |
| 2004/0044087 A1 | 3/2004 | Maye |
| 2004/0087808 A1 * | 5/2004 | Prevost et al. ................ 554/9 |
| 2004/0226451 A1 * | 11/2004 | Diaz ............................ 99/276 |

* cited by examiner

*Primary Examiner* — Walter D Griffin
*Assistant Examiner* — Shanta G Doe
(74) *Attorney, Agent, or Firm* — Crossley Patent Law; Mark A. Crossley

(57) ABSTRACT

An ethanol distillation system that aims to increase the yield from an ethanol distillation process from 17 percent to a number approaching 100 percent through the use of a series of P-traps, condensers, heaters and coolers. A series of 4 P-traps are placed in-line in relation to one another, with exit lines exiting each P-trap. Each P-trap has its own pair of heating elements and a single distillation apparatus, with the distillation apparatus condensing evaporated alcohol into liquid form and placing it into the exit line so it can be collected. Any liquids left over after it has passed through the series of 4 P-traps and a cold condenser will enter into a return pipe to be reused by the yeast in this process.

4 Claims, 2 Drawing Sheets

ETHANOL DISTILLATION SYSTEM

BACKGROUND OF THE INVENTION

The present invention concerns that of a new and improved ethanol distillation system that aims to increase the yield from an ethanol distillation process from 17 percent to a number approaching 100 percent through the use of a series of P-traps, condensers, heaters and coolers.

SUMMARY OF THE INVENTION

The present invention concerns that of a new and improved ethanol distillation system that aims to increase the yield from an ethanol distillation process from 17 percent to a number approaching 100 percent through the use of a series of P-traps, condensers, heaters and coolers. A series of 4 P-traps are placed in-line in relation to one another, with exit lines exiting each P-trap. Each P-trap has its own pair of heating elements and a single distillation apparatus, with the distillation apparatus condensing evaporated alcohol into liquid form and placing it into the exit line so it can be collected. Any liquids left over after it has passed through the series of 4 P-traps will enter into a return pipe to be reused by the yeast in this process.

There has thus been outlined, rather broadly, the more important features of an ethanol distillation system that the detailed description thereof that follows may be better understood and in order that the present contribution to the art may be better appreciated. There are, of course, additional features of the ethanol distillation system that will be described hereinafter and which will form the subject matter of the claims appended hereto.

In this respect, before explaining at least one embodiment of the ethanol distillation system in detail, it is to be understood that the ethanol distillation system is not limited in its application to the details of construction and to the arrangements of the components set forth in the following description or illustrated in the drawings. The ethanol distillation system is capable of other embodiments and being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the ethanol distillation system. It is important, therefore, that the claims be regarded as including such equivalent constructions insofar as they do not depart from the spirit and scope of the present invention.

It is therefore an object of the present invention to provide an ethanol distillation system which has all of the advantages of the prior art and none of the disadvantages.

It is another object of the present invention to provide an ethanol distillation system which may be easily and efficiently manufactured and marketed.

It is another object of the present invention to provide an ethanol distillation system which is of durable and reliable construction.

It is yet another object of the present invention to provide an ethanol distillation system which is economically affordable and available for relevant market segment of the purchasing public.

Other objects, features and advantages of the present invention will become more readily apparent from the following detailed description of the preferred embodiment when considered with the attached drawings and appended claims.

DESCRIPTION OF THE PREFERRED EMBODIMENT

Figure 1:
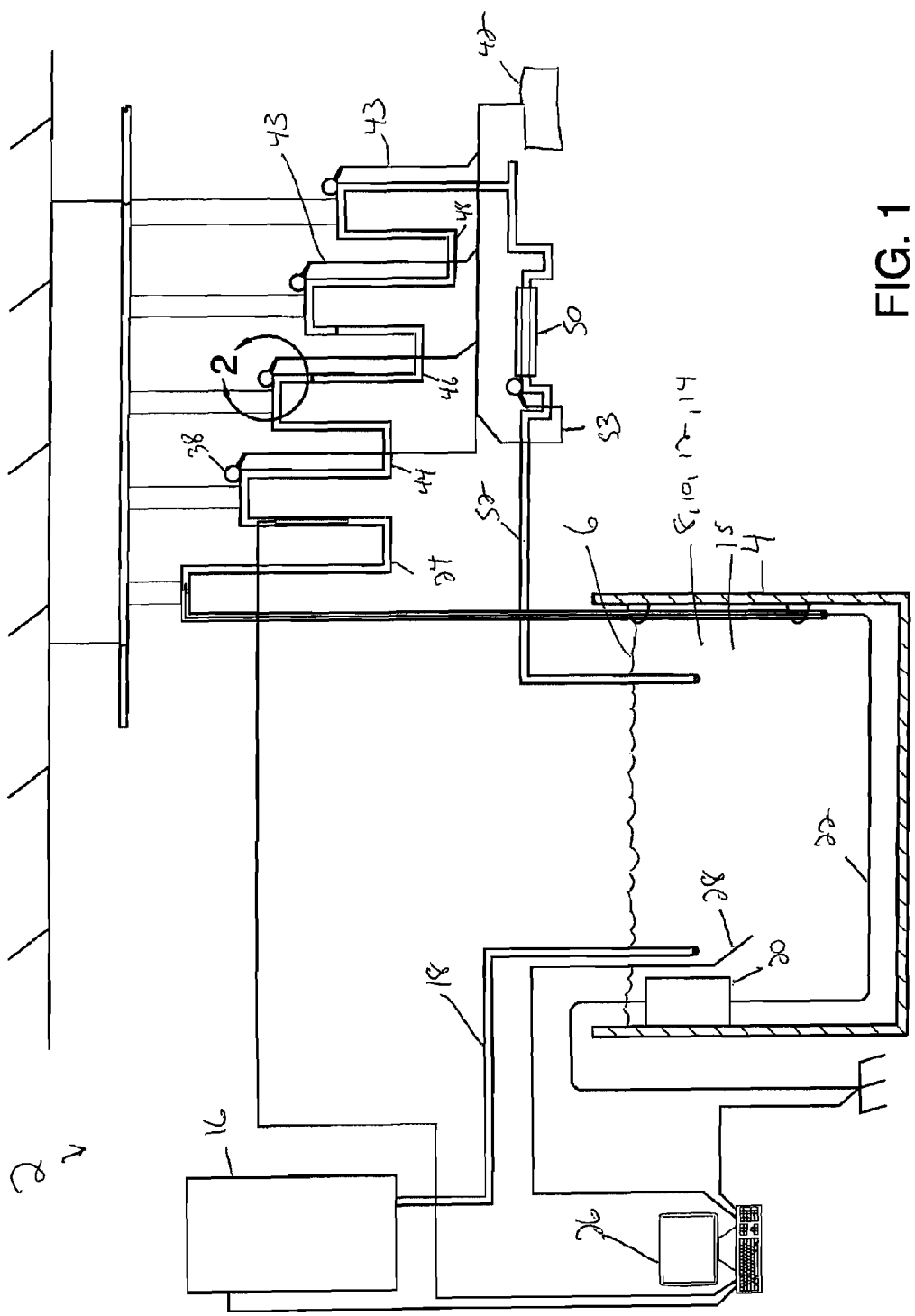
FIG. 1 shows a side view of all of the equipment used with the ethanol distillation system.
Figure 2:
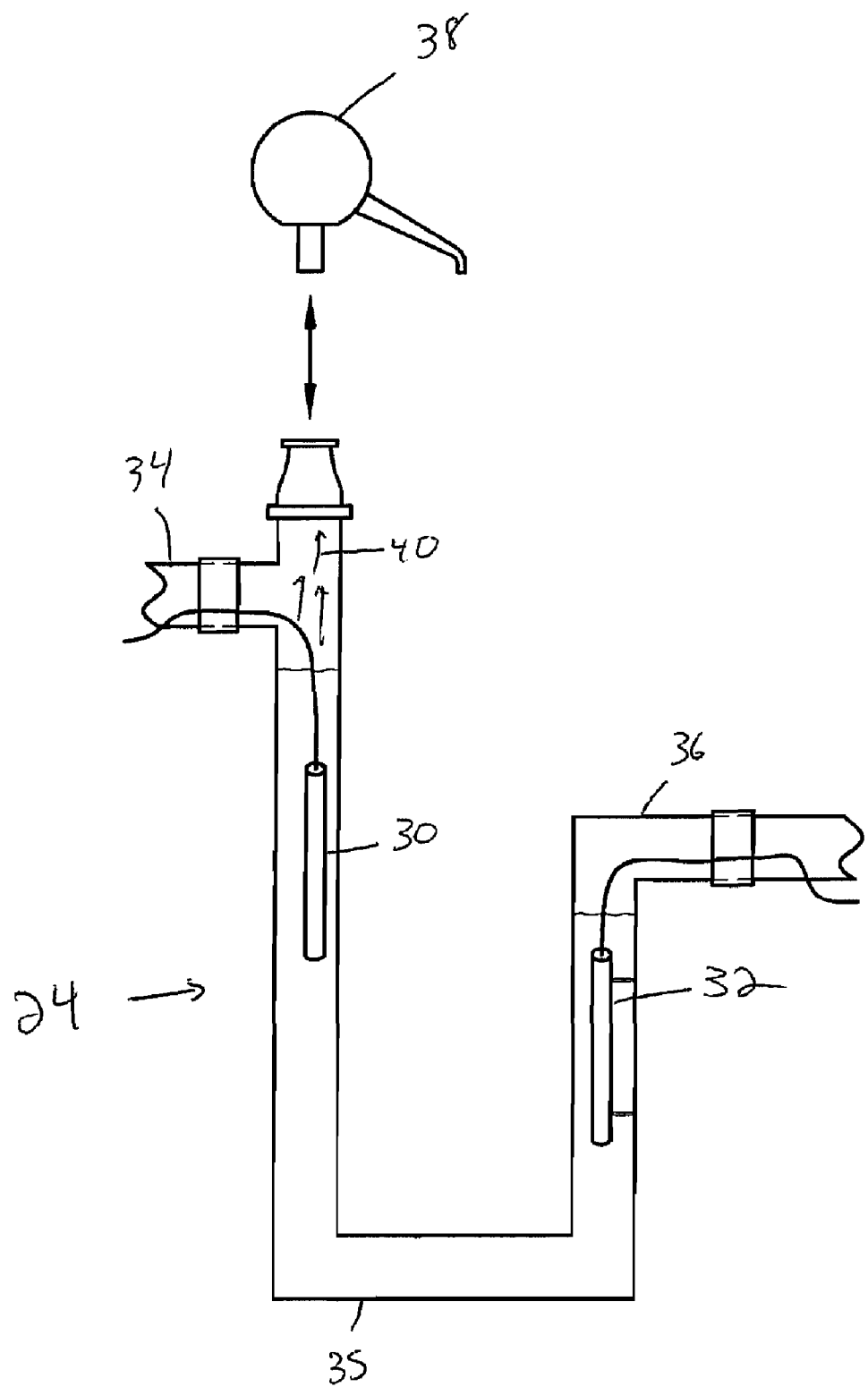
FIG. 2 shows a side view of a P-trap portion of the ethanol distillation system.

With reference now to the drawings, and in particular to FIGS. 1 through 2 thereof, a new ethanol distillation system embodying the principles and concepts of the present invention and generally designated by the reference numeral 2 will be described.

As best illustrated in FIGS. 1 through 6, the ethanol distillation system 2 comprises a fermentation container 4 in which an ongoing fermentation reaction is ongoing all the time. The fermentation container 4 includes a fermentation mixture 6, with the fermentation mixture 6 comprising an amount of water 8, an amount of yeast 10, and an amount of food 12 for the yeast 10 to react with, and an amount of micronutrients 14 for the yeast 10 to maintain their vitality on an ongoing basis. The food 12 is preferably a premium food that does not include any starches.

The food 12 is normally located within a container 16 that is located above and adjacent to the fermentation container 4, with the food 12 passing through a hose 18 to travel from the container 16 to the fermentation container 4.

A pump 20 is located within the fermentation container 4 and is normally located underwater within the fermentation mixture 6. The pump 20, on an ongoing basis, pumps the fermentation mixture 6 out of the fermentation container 4 through a pump hose 22 into a P-trap 24. The flow rate of the pump 20 is controlled on an ongoing basis because if the flow rate of the liquid exiting the pump 20 is too fast, not enough ethanol would be extracted from the system 2, while if the flow rate of the liquid exiting the pump 20 is too slow, electricity would be wasted. Preferably, the pump is designed to flow at a rate between 70 to 250 gallons per hour.

A computer 26 is also used with the system 2 to help measure several variables on an ongoing basis. The computer 26 is connected to a probe 28 that is located within the fermentation container 4 that monitors several variables on an ongoing basis, such as pH, temperature, specific gravity, and other variables. Furthermore, the computer 26 is connected to the pump 20 so that it can control the flow rate of the fermentation mixture 6 exiting the pump 20 based upon a number of measured variables.

Once the fermentation mixture 6 enters the P-trap 24, a pair of submersible electric heaters 30 and 32 are generally submerged within the volume of fermentation mixture 6 within the P-trap 24. These heaters 30 and 32 cause the fermentation mixture 6 to be heated to the temperature of ninety (90) degrees. Heater 30 is closer to the incoming line 34 than the heater 32, which is closer to the outgoing line 36. A P-trap line 35 connects the incoming line 34 of each P-trap to the outgoing line 36.

A distillation apparatus 38 is attached to the P-trap 24 above the location of the heater 30. The alcohol within the fermentation mixture 6, which has a lower boiling point than the water within the fermentation mixture 6, would partially evaporate when coming into contact with the heater 30. This evaporate 40 then enters into the distillation apparatus 38, where it is distilled (condensed). The distillate then passes through a distillation collection line and is forwarded into a holding container 42 to be redistilled and denatured further.

After the fermentation mixture 6 exited the outgoing line 36 of the P-trap 24, the fermentation mixture 6 passes through a series of three additional P-traps 44, 46, and 48, which are lined up in a row. Each of these P-traps 44, 46, and 48 have the same configuration as in the P-trap 24, causing additional amounts of alcohol 15 to be evaporated out of the fermentation mixture 6, condensed by an attached distilled apparatus 38, and then forwarded on to a subsequent P-trap.

After the fermentation mixture 6 has passed through the P-trap 48, which is the last P-trap in the line of four successive P-traps, the fermentation mixture 6 then subsequently passes through a cold condenser 50 in an effort to return all of the fermentation mixture 6 to liquid form before it is placed back in the fermentation container 4 via a return line 52. The cold condenser 50 also will condense out any ethanol 15 separately and will forward this ethanol 15 to a holding container 42. The return line 52 travels all the way from the holding container 42 to the fermentation container 4, where the fermentation mixture 6 is then deposited for further processing.

The system and process disclosed herein is designed to produce more ethanol by requiring less sugar and nutrients per gallon of ethanol. Theoretically, the current method would produce only 1,700 gallons of ethanol per 10,000 gallons of mash. The system and process disclosed herein is designed to increase the yield from 17 percent to 100 percent so that for every gallon of ethanol removed from the fermentation container, a gallon of nutrients would be added.

With respect to the above description then, it is to be realized that the optimum dimensional relationships for the parts of the present vehicle air freshener device to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What I claim as my invention is:

1. An ethanol distillation system comprising
    a fermentation container,
    a fermentation mixture located within the fermentation container,
    means for pumping the fermentation mixture out of the fermentation container,
    means for distilling the fermentation mixture,
    means for collecting the distillate from the fermentation mixture,
    wherein the fermentation mixture located within the fermentation container further comprises
        a volume of water,
        a volume of yeast placed within the volume of water,
        a volume of food placed within the volume of water,
        an amount of micronutrients placed within the volume of water,
    wherein the ethanol distillation system further comprises
        means for delivering the volume of food into the fermentation container,
    wherein the means for delivering the volume of food into the fermentation container further comprises
        a food container located above the fermentation container, the food container including some of the volume of food,
        a hose traveling from the food container to the fermentation container,
        wherein some of the food of the volume of food will travel from the food container down into the fermentation container,
    wherein the means for pumping the fermentation mixture out of the fermentation container further comprises
        a pump located within the fermentation container, the pump normally being located below the top of the volume of water within the fermentation container,
        a pump hose, the pump hose being connected to the pump,
        means for controlling the rate at which the pump pumps fermentation mixture out of the fermentation tank,
    wherein the means for controlling the rate at which the pump pumps fermentation mixture out of the fermentation tank further comprises
        a probe located within the fermentation tank,
        a computer, the computer being connected to the probe,
        wherein the probe measures several variables of the fermentation mixture on an ongoing basis,
        further wherein the computer controls the rate of pump flow through the pump by using feedback from the probe,
    a plurality of P-traps,
    wherein each P-trap further comprises
        an incoming line,
        a P-trap line attached to the incoming line,
        an outgoing line attached to the P-trap line,
        a pair of heating elements comprising a first heating element and a second heating element, wherein both heating elements are located within the P-trap line,
    wherein a means for distilling the fermentation mixture is attached to each of the plurality of P-traps above a location of at least one of the heating elements of the P-trap,
    wherein the first heating element is located closer to the incoming line than the outgoing line, and further wherein the second heating element is located closer to the outgoing line than the incoming line,
    further wherein the heating elements cause some of the alcohol within the fermentation mixture to evaporate, thereby creating an evaporative distillate,
    further wherein the evaporative distillate enters in to the distillation apparatus and is condensed.

2. An ethanol distillation system according to claim 1 wherein the means for collecting the distillate from the fermentation mixture further comprises
    (a) a holding container,
    (b) a plurality of distillation collection lines,
    (c) wherein each distillation collection line is connected to one distillation apparatus,
    (d) further wherein each distillation collection line is also connected to the holding container,
    (e) further wherein evaporative distillate collected within each distillation apparatus passes through the respective distillation collection line onward to the holding container.

3. An ethanol distillation system according to claim 2 wherein the ethanol distillation system further comprises means to reduce the fermentation mixture to the fermentation tank to a liquid form.

4. An ethanol distillation system according to claim 3 wherein the means to reduce the fermentation mixture to the fermentation tank to a liquid form further comprises
 (a) a return line, the return line connected to the holding container, the return line also connected to the fermentation tank,
 (b) a cold condenser being attached to the return line,
 (c) a distillation collection line attached to the cold condenser, the distillation collection line also being attached to the holding container,
 (d) wherein the cold condenser condenses any remaining gases within the fermentation mixture to liquid form,
 (e) further wherein the cold condenser condenses out any ethanol in the evaporative distillate still remaining in the fermentation mixture and passes this distillate to the holding container through an attached distillation collection line.

\* \* \* \* \*